(12) United States Patent
Sanso et al.

(10) Patent No.: US 8,853,727 B1
(45) Date of Patent: Oct. 7, 2014

(54) LIGHT EMITTING DIODE CABLE AND HEAT SINK

(71) Applicants: David Sanso, Golden, CO (US); Mason Williams, Golden, CO (US); Brent Hymel, Golden, CO (US); Aaron Pitzer, Golden, CO (US)

(72) Inventors: David Sanso, Golden, CO (US); Mason Williams, Golden, CO (US); Brent Hymel, Golden, CO (US); Aaron Pitzer, Golden, CO (US)

( * ) Notice: Subject to any disclaimer, the term of this patent is extended or adjusted under 35 U.S.C. 154(b) by 0 days.

(21) Appl. No.: 13/711,073

(22) Filed: Dec. 11, 2012

Related U.S. Application Data

(60) Provisional application No. 61/570,663, filed on Dec. 14, 2011, provisional application No. 61/583,273, filed on Jan. 5, 2012.

(51) Int. Cl.
*H01L 29/22* (2006.01)

(52) U.S. Cl.
USPC .................................... 257/98; 257/E29.099

(58) Field of Classification Search
USPC ............................................................ 257/98
See application file for complete search history.

(56) References Cited

U.S. PATENT DOCUMENTS 7,489,840 B2 * 2/2009 Sekiya et al. .................... 385/36

* cited by examiner

*Primary Examiner* — Thanh Nguyen
(74) *Attorney, Agent, or Firm* — Luis Figarella

(57) ABSTRACT

A high output light emitting diode (LED) based lighting module includes a plurality of LEDs on a substrate board, a fiber optic mounting assembly that securely holds a plurality of fiber bundles that form a fiber cable to said LEDs so that each LED mates to a fiber bundle making each fiber bundle slightly overlap the active area of its respective LED and mechanical means for holding each fiber optic bundle a fixed distance from said LED substrate.

8 Claims, 8 Drawing Sheets

LIGHT EMITTING DIODE CABLE AND HEAT SINK

CROSS-REFERENCE TO RELATED APPLICATIONS

This application claims priority to U.S. provisional patent applications Ser. No. 61/570,663 titled "Light Emitting Diode Cable" filed on Dec. 14, 2011, and Ser. No. 61/583,273 titled "Connector LED Heatsink" filed on Jan. 5, 2012 the disclosure of which is herein incorporated by reference in their entirety.

PATENTS CITED

The following documents and references are incorporated by reference in their entirety, Savage, Jr., (U.S. Pat. No. 5,548,676), Wehner (U.S. Pat. No. 7,086,765), Ruffin (U.S. Pat. No. 7,182,496), Gingrich, III et al (U.S. Pat. No. 7,942,563), Simon et al (U.S. Pat. No. 8,256,924) and Huang (U.S. Pat. Appl. No. 2012/0194071).

FIELD OF THE INVENTION

The present invention relates generally to the field of light emitting diodes and of efficient ways to remove the heat generated by their operation. More specifically, the present invention is directed to a lighting device that allows for the use of multiple LEDs to be efficiently coupled with a light fiber bundle or cable in order to create high output lighting and efficiently removes the heat generated by these LEDs while maintaining a good optical coupling.

DESCRIPTION OF THE RELATED ART

Light emitting diodes (LEDs) are well known solid state light sources. LEDs have many advantages over traditional lighting sources such as incandescent bulbs and Compact Fluorescent bulbs (CFLs), as they are cheaper to produce, more robust and are more efficient in their use of power, typically requiring less power to generate the same amount of light. Because they are solid state devices, they are especially desirable as they emit light with high power efficiency over specific and customizable colors of the spectrum. A major problem of LEDs is that they are not focused light sources and suffer from relatively low light output. These shortcomings prevent application of LEDs in uses where high light intensity is desired.

There are many commercial applications requiring high light output, in particular in medical applications, where the above advantages are desired. For example, there is a great demand for LED light sources to replace the traditional halogen and other incandescent sources that are used in conjunction with optical fibers to deliver illumination within a body cavity.

When using LED/LED's to illuminate an optical fiber, the light output through the fiber drops off 5% per foot. Given a standard 8 Ft cable the LED light drops off by 30% from the LED to the end of the fiber. The closer the LED can be placed to the end of the fiber, the more efficient the overall system will be. A major problem when placing the LED at the end or close to the end of the fiber is the concentration of heat next to the camera head or the user. A few watts of heat can cause discomfort or affect the performance of the camera. While each LED by itself dissipates a small amount of heat, putting them in a small concentrated space can cause significant heat.

Of course, in any of these applications, there is a need to remove heat. Removing the heat from an LED array while maintaining good optical coupling in a removable system can be a challenge. In a camera system where the surgeon has to hold the camera in their hand, it would be uncomfortable to include the LEDs in the camera head due to the heat generated by the LEDs and their associated power electronics.

While the LEDs are an efficient form of generating light, there is still a fair amount of heat generated by an array of LEDs. Given the small active area of the LED and the precision at which they must be aligned, placing the LEDs in an enclosure and removing the heat from the enclosure will prohibit repeatable optical coupling between the light carrying fiber and the LEDs causing demised light output.

Thus, there is a need for an LED based device which provides sufficient light intensity for high lighting applications while at the same time efficiently removing the heat generated. There is a further need for an LED based device which allows light output to be focused and directed into the fiber optic assembly so that it allows for high light output from the end of an optic fiber.

SUMMARY OF THE INVENTION

This section is for the purpose of summarizing some aspects of the present invention and to briefly introduce some preferred embodiments. Simplifications or omissions may be made to avoid obscuring the purpose of the section. Such simplifications or omissions are not intended to limit the scope of the present invention.

In one aspect the invention is about a high output light emitting diode (LED) based lighting module, comprising an LED substrate board having two or more LEDs mechanically mounted onto at least one face of said substrate board, a fiber optic mounting assembly having two or more slot assemblies, each said slot assembly having a through opening, said opening going from the front face of said mounting assembly to the back face of said slot assembly, with each said opening designed to securely hold a light fiber bundle so that two or more of the ends of said fiber bundles located at said back face of said mounting assembly present a uniform surface whose profile mates with two or more of the LEDs mounted on said LED substrate, so that each light fiber bundle slightly overlaps the active area of the respective LED it is mated to and mechanical means for holding said fiber optic mounting assembly at a fixed distance from said LED substrate.

In another aspect, the invention is about said electrical connections interfacing said LEDs mounted on said LED substrate through said substrate board to a suitable electrical connector, a heat sink assembly is mechanically attached to said LED substrate, a housing and a light fiber cable formed from two or more light fiber bundles. In yet another aspect, the invention is about said lighting module comprising a base station.

In yet another aspect, the invention is about a high output light emitting diode (LED) based lighting module, comprising a housing, a light fiber cable formed from two or more light fiber bundles and a fiber optic mounting assembly having two or more slot assemblies, each said slot assembly having a through opening, said opening going from the front face of said mounting assembly to the back face of said slot assembly, with each said opening designed to securely hold a light fiber bundle so that two or more of the ends of said fiber bundles located at said back face of said mounting assembly present a uniform surface.

In another aspect, the invention is about a base station housing a heat sink attached to an LED substrate board having two or more LEDs mechanically mounted onto at least one face of said substrate board and electrical connections interfacing at least two said LEDs mounted on said LED substrate through said substrate board to a suitable electrical source within said base station, mechanical means for holding said fiber optic mounting assembly at a fixed distance from said LED substrate, so that the profile of the back face of two or more of said fiber optic whose profile mates with two or more of the LEDs mounted on said LED substrate, so that each light fiber bundle slightly overlaps the active area of the respective LED it is mated to, and mechanical means for disconnecting said module from said base station.

Other features and advantages of the present invention will become apparent upon examining the following detailed description of an embodiment thereof, taken in conjunction with the attached drawings.

The above-described and other features will be appreciated and understood by those skilled in the art from the following detailed description, drawings, and appended claims.

DETAILED DESCRIPTION OF THE PREFERRED EMBODIMENT

To provide an overall understanding of the invention, certain illustrative embodiments and examples will now be described. However, it will be understood by one of ordinary skill in the art that the same or equivalent functions and sequences may be accomplished by different embodiments that are also intended to be encompassed within the spirit and scope of the disclosure. The compositions, apparatuses, systems and/or methods described herein may be adapted and modified as is appropriate for the application being addressed and that those described herein may be employed in other suitable applications, and that such other additions and modifications will not depart from the scope hereof.

All references, including any patents or patent applications cited in this specification are hereby incorporated by reference. No admission is made that any reference constitutes prior art. The discussion of the references states what their authors assert, and the applicants reserve the right to challenge the accuracy and pertinence of the cited documents. It will be clearly understood that, although a number of prior art publications are referred to herein, this reference does not constitute an admission that any of these documents form part of the common general knowledge in the art It is acknowledged that the term 'comprise' may, under varying jurisdictions, be attributed with either an exclusive or an inclusive meaning. For the purpose of this specification, and unless otherwise noted, the term 'comprise' shall have an inclusive meaning—i.e. that it will be taken to mean an inclusion of not only the listed components it directly references, but also other non-specified components or elements. This rationale will also be used when the term 'comprised' or 'comprising' is used in relation to one or more steps in a method or process.

Figure 1:
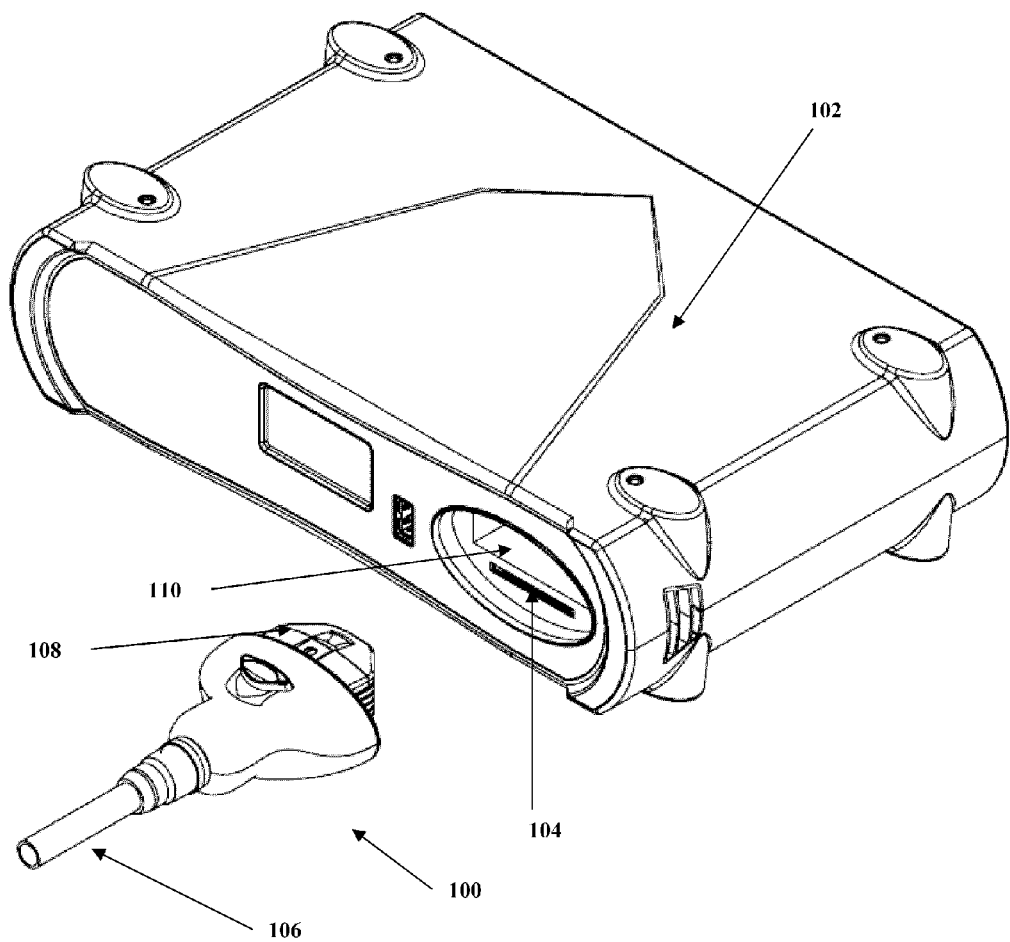
FIGS. 1-2 show isometric illustrations of a detachable Fiber Cable light source utilizing multi-LEDs and a heat sink, according to an exemplary embodiment of the invention.
Figure 2:
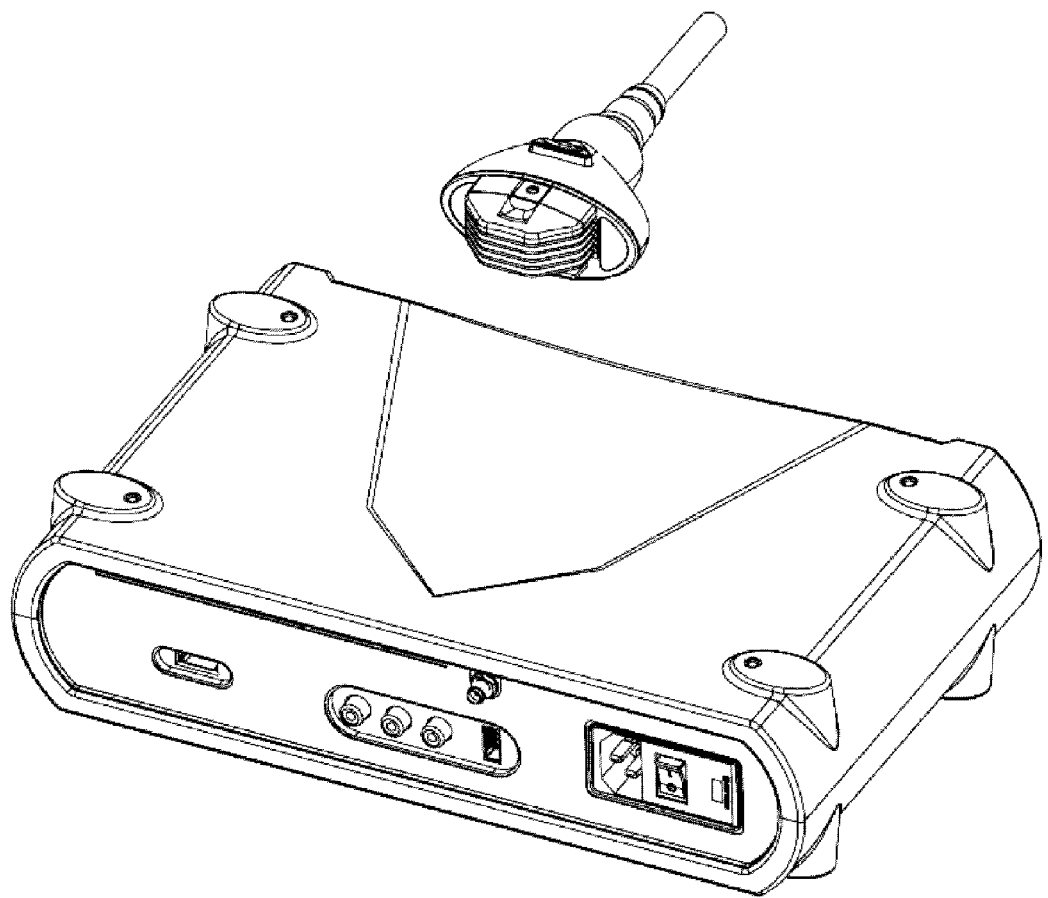

Referring to FIG. 1 we see an embodiment of an multi-LED light source having two portions, a light fiber cable interface module 100 designed to hold a light fiber cable 106 and to nestle and be powered by a base station 102. Such an arrangement is very common in the medical field, for among other things it allows for any contamination within the interface module 100 to allow for its replacement/sterilization without disposing of the higher cost base station 102. In addition, the base station 102 contains all medical grade AC power supplies, and the module only has within the electronic interface slot 104 safe DC voltage signals.

In one embodiment, the LEDs are housed within the module 100 and thus the heat from the LEDs must be removed from within its housing. This is accomplished by a heat sink 108 in thermal contact with the electronics within the module 100. The heat sink is then housed within a heat removal opening 110 in the base station 102, allowing for efficient cooling of the electronics within the module 100.

In one embodiment, said heat removal may be accomplished by appropriate thermal transfer from the module heat sink to a similar of larger unit within the base station 102, or by passing air or any appropriate fluid over the heat sink fins within the opening 110. Alternate embodiments may use Peltier thermo electric cooling and/or any other suitable heat removal technique.

Figure 3:
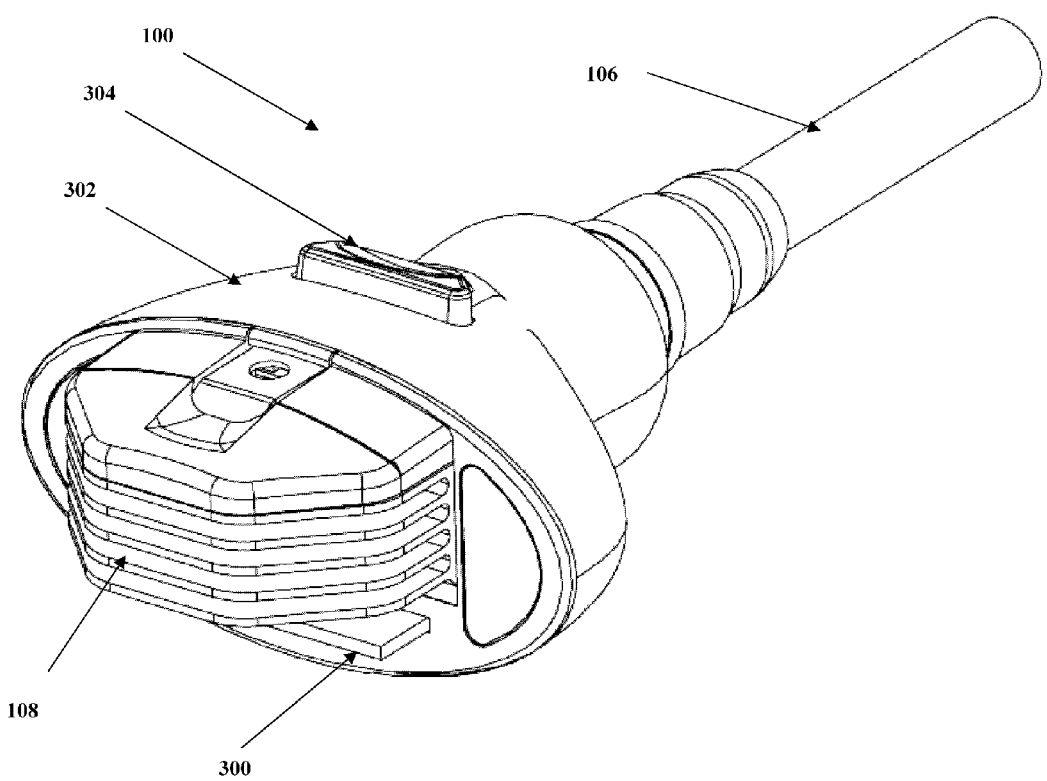
FIG. 3 shows an illustration of the back of a high output multi-LED lighting device, according to an exemplary embodiment of the invention.
Figure 4:
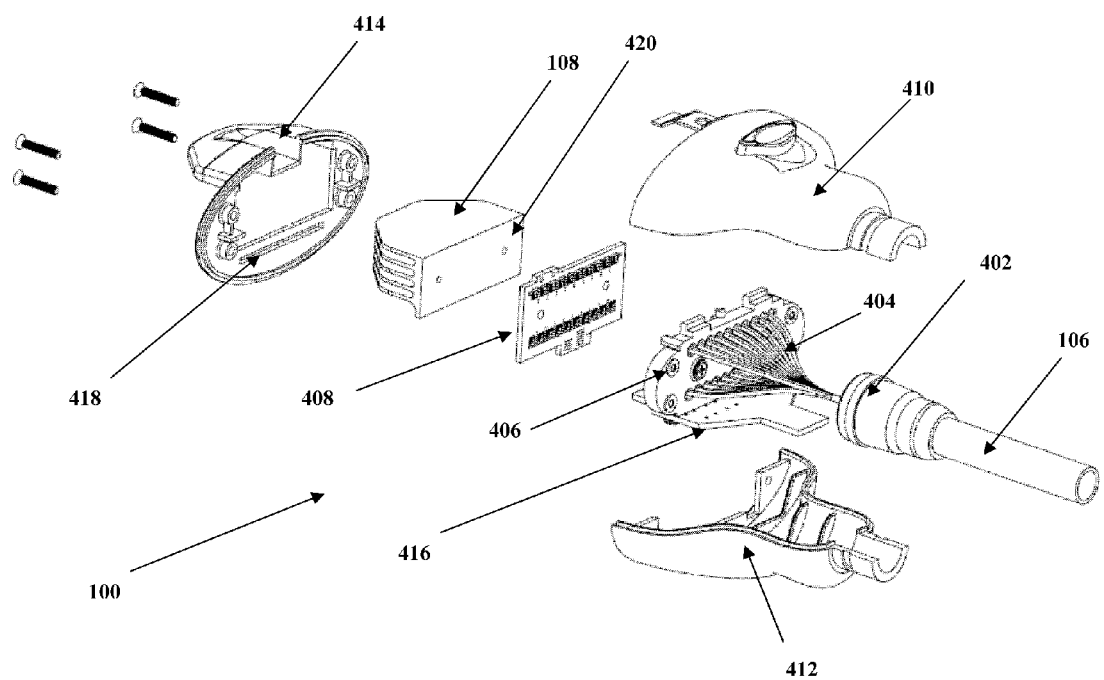
FIG. 4 shows an exploded view of the interior of the high output multi-LED lighting device, according to an exemplary embodiment of the invention.

Referring to FIG. 3, we see the back isometric view of the interface module 100, with details of the heat sink 108 and the interface electronics connector 300 designed to mate within the electronic interface slot 104. The signals interfaced include control and power signals to all the LED electronics, as well as suitable status signals regarding the failure of any electronics (e.g. LEDs, etc.). In one embodiment, the unit is released from the body 102 by pressing on the release button 304.

In one embodiment, (FIGS. 4-8), the interface module 100 is comprised of a fiber optic cable 106, whose housing 302 is formed by a front piece 402, a top 410, and bottom 412 and a back piece 414. In alternate embodiments, this housing may be a single piece, two pieces and or any number of combinations. In one embodiment, the interior cavity of the housing is completely sealed against fluid penetration. In an alternate embodiment, it is made resistant to fluids, so that only prolonged immersion results in contamination.

In one embodiment, within the housing cavity we find the fiber cable 106, itself formed of two or more light fiber strand bundles 404. As seen in the isometric back view 800 of the back face 806 of the fiber optic mounting assembly 406, each of the fiber bundles 404 bundles is individually guided and secured to an opening within a fiber bundle holding slot 808. These slots 808 each secures and holds a fiber bundle 404 for mating with an LED 602, so that the area of the fiber bundle 404 overlays the LED active light emitting area 604. In this fashion 502 light losses are minimized.

In one embodiment, the LEDs 602 being used are devoid of any and all lensing on its surface, allowing for a perfect match of the flat surface at the end of the fiber 804 with that on top of the LED active light emitting area. In alternate embodiments, lensing on top of the LED active emitting area 604 might be suitable and conformably matched with the end of the fiber 804 by matching the machining performed on both the end 804 and the back face 802 of the fiber holding slot assembly 808.

Appropriate mating of the back face 806 of the fiber optic mounting assembly 406 is accomplished by ensuring that the plane formed by the back face 802 ends of two or more slot assemblies 808 match the plane formed by the upper surface of the light emitting area 604 of the respective or matching two or more LEDs 602 on one face of the LED substrate 408. Something easy to specify based on the tolerances of the manufacturing process of each.

In one embodiment, each fiber bundles 404 is securely attached within the slot assembly 808 opening by attaching it through chemical means, including gluing using optical epoxy. In an alternate embodiment, they may be screwed in, compressed fitted, or through any suitable mechanical means.

Figure 5:
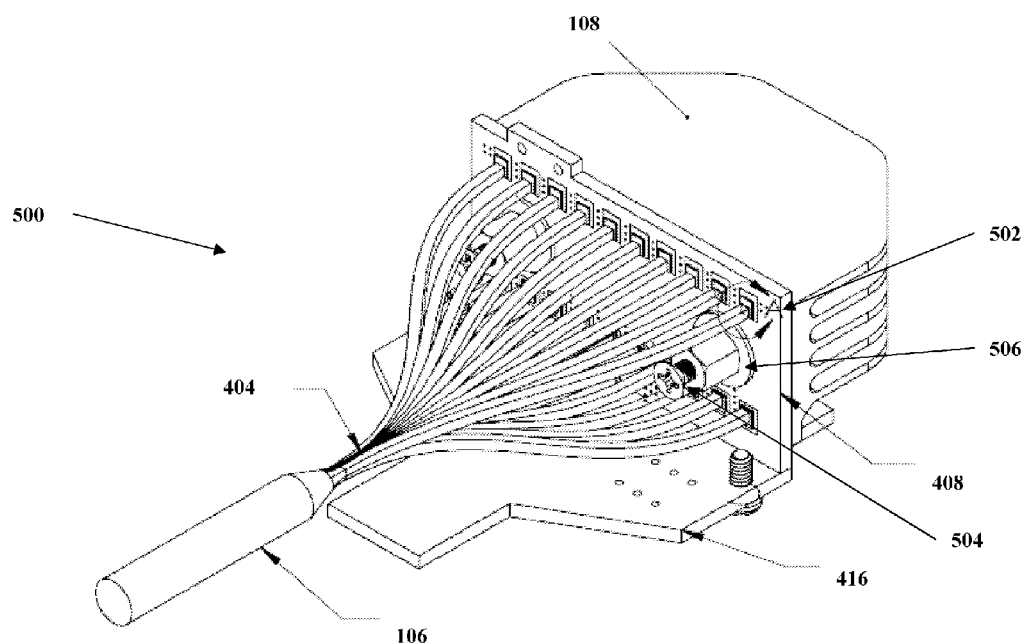
FIGS. 5-8 show various illustrations of the components within the multi-LED lighting device, according to an exemplary embodiment of the invention.
Figure 6:
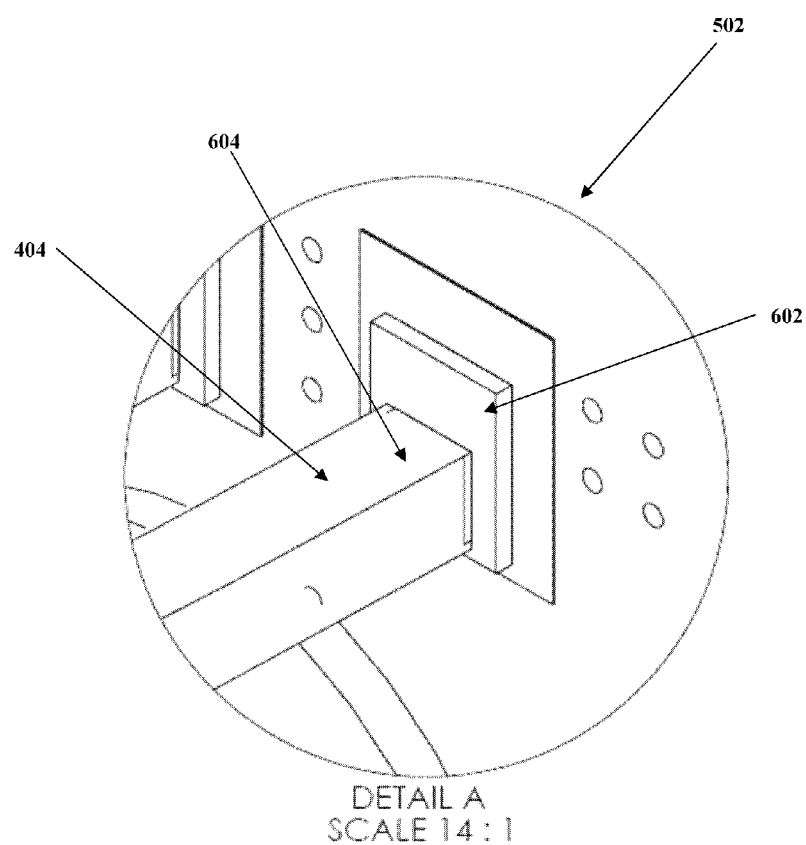
Figure 7:
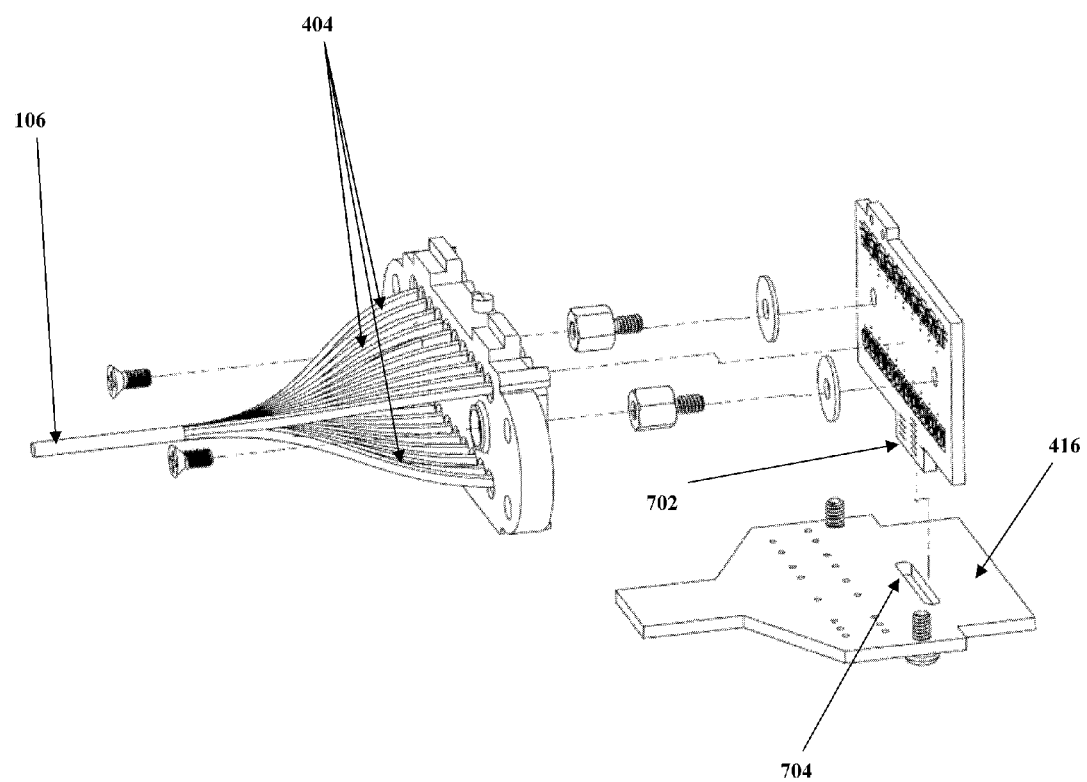
Figure 8:
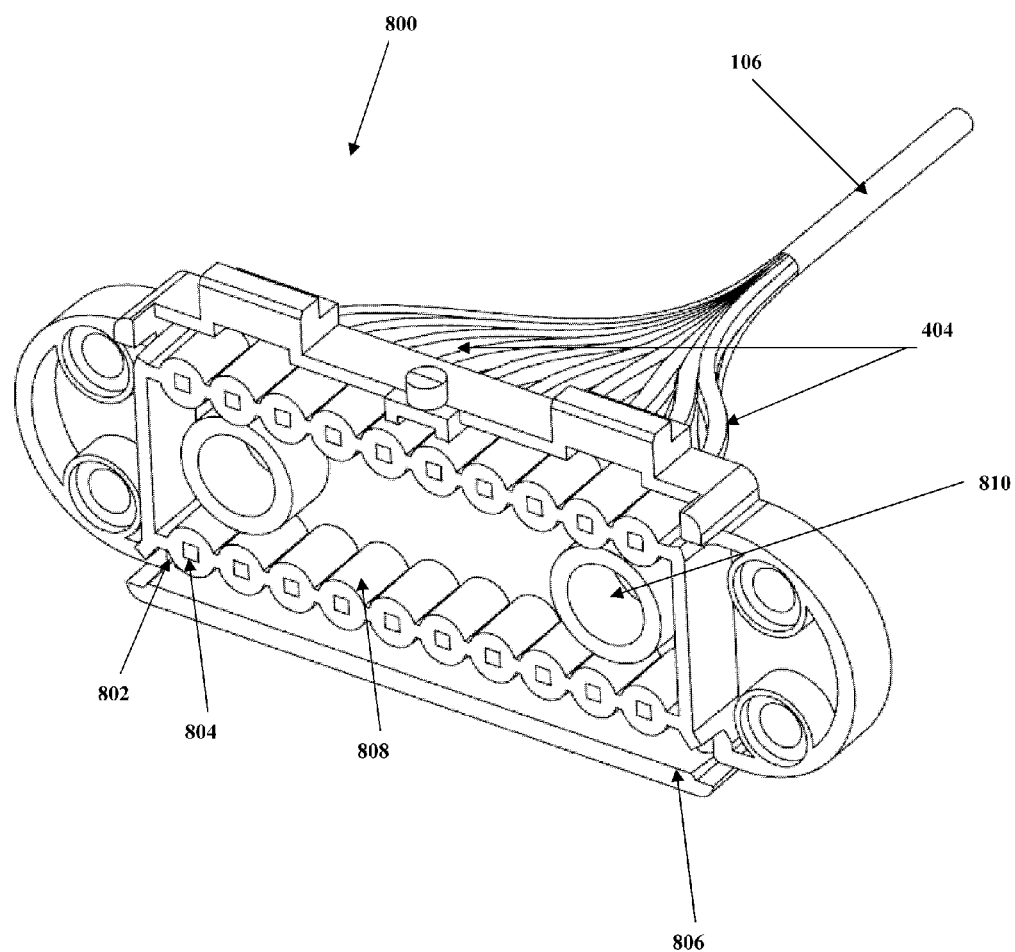

The view illustrated 500 in FIGS. 5-6 omits the fiber optic mounting assembly 406 in order to illustrate how the fiber bundles 404 rest on the LEDs 602. Of course, in practice, this matching is accomplished by attaching the fiber optic mounting assembly 406 to the LED substrate board 408 via at least two screws 504 (one on each side), which attaches to the offset nut 506, which itself goes into the nut recess opening 810.

In one embodiment, the heat sink 108 is securely attached to the back of the LED substrate board 408 via pressing contact. This force is provided by the screws 504 going into the matching threads of the heat sink screw holes 420. This allows for the tight pressing of the heat sink 108 surface against the back face of the LED substrate 408, maximizing the heat transfer. In an alternate embodiment, any and all heat transfer solutions may be used. These include the use of thermal transfer paste or glue between the LED substrate 408 and the heat sink 108, etc.

In one embodiment, the LED substrate 408 is a PCB (Printed Circuit Board) with internal and external electric signal routings. These are communicated to the base station via a connection to the supporting substrate board 416 which then routes these connections to the connector 300 which interfaces to the base station. In alternate embodiments, the connection may be routed using flex circuits, direct cables, insertion connectors, etc.

In an alternate embodiment, the housing is designed so that the heat sink 108 and the LED substrate 408 remain connected to the base station 102, and when the disconnect button 304 is pressed, the Fiber optic mounting assembly 406 releases from the LED substrate 108. Such an approach would not obviate the screw 504 attachment to the mounting assembly 406, substituting it for a clamp connected to the button 304. Since the assembly 406 and forward portions require no electrical interfacing, all the substrate boards could remain connected to the base station 102.

CONCLUSION

In concluding the detailed description, it should be noted that it would be obvious to those skilled in the art that many variations and modifications can be made to the preferred embodiment without substantially departing from the principles of the present invention. Also, such variations and modifications are intended to be included herein within the scope of the present invention as set forth in the appended claims. Further, in the claims hereafter, the structures, materials, acts and equivalents of all means or step-plus function elements are intended to include any structure, materials or acts for performing their cited functions.

It should be emphasized that the above-described embodiments of the present invention, particularly any "preferred embodiments" are merely possible examples of the implementations, merely set forth for a clear understanding of the principles of the invention. Any variations and modifications may be made to the above-described embodiments of the invention without departing substantially from the spirit of the principles of the invention. All such modifications and variations are intended to be included herein within the scope of the disclosure and present invention and protected by the following claims.

The present invention has been described in sufficient detail with a certain degree of particularity. The utilities thereof are appreciated by those skilled in the art. It is understood to those skilled in the art that the present disclosure of embodiments has been made by way of examples only and that numerous changes in the arrangement and combination of parts may be resorted without departing from the spirit and scope of the invention as claimed. Accordingly, the scope of the present invention is defined by the appended claims rather than the forgoing description of embodiments.

The invention claimed is:

1. A high output light emitting diode (LED) based lighting module, comprising:
    an LED substrate board having two or more LEDs mechanically mounted onto at least one face of said substrate board;
    a fiber optic mounting assembly having two or more slot assemblies, each said slot assembly having a through opening, said opening going from the front face of said mounting assembly to the back face of said slot assembly, with, each said opening designed to securely hold a light fiber bundle so that two or more of the ends of said fiber bundles located at said back face of said mounting assembly present a uniform surface so the individual profile of each individual fiber end mates with an individual LED mounted on said LED substrate, so that each light fiber bundle slightly overlaps the active area of the respective LED it is mated to; and
    mechanical means for holding said fiber optic mounting assembly at a fixed distance from said LED substrate.

2. the lighting module of claim 1 further comprising;
    electrical connections interfacing said LEDs mounted on said LED substrate through said substrate board to a suitable electrical connector;
    a heat sink assembly is mechanically attached to said LED substrate;
    a housing; and
    a light fiber cable formed from two or more light fiber bundles.

3. the lighting module of claim 2 further comprising;
    a base station.

4. the lighting module of claim 2 wherein;
    said mechanical means for holding said fiber optic mounting assembly at a fixed distance from said LED substrate are comprised of a screw and offset nut combination.

5. the lighting module of claim 1 wherein;
    said mechanical means for holding said fiber optic mounting assembly at a fixed distance from said LED substrate are comprised of a screw and offset nut combination.

6. A high output light emitting diode (LED) based lighting module, comprising:
    a housing;
    a light fiber cable formed from two or more light fiber bundles; and
    a fiber optic mounting assembly having two or more slot assemblies, each said slot assembly having a through opening, said opening going from the front face of said mounting assembly to the back face of said slot assembly, with each said opening designed to securely hold an individual light fiber bundle so that two or more of the ends of said fiber bundles located at said back face of said mounting assembly present collectively a uniform surface.

7. the lighting module of claim 6 further comprising;
a base station housing a heat sink attached to an LED substrate board having two or more LEDs mechanically mounted onto at least one face of said substrate board and electrical connections interfacing at least two said LEDs mounted on said LED substrate through said substrate board to a suitable electrical source within said base station;
mechanical means for holding each said fiber optic mounting assembly at a fixed distance from its corresponding each said LED substrate, so that the profile of the back face of two or more of said individual fiber optic bundles whose profile mates with a respective two or more of the LEDs mounted on said LED substrate, and so that each light fiber bundle slightly overlaps the active area of the respective LED it is mated to; and
mechanical means for disconnecting said module from said base station.

8. the lighting module of claim 7 wherein;
said mechanical means for holding each said fiber optic mounting assembly at a fixed distance from its corresponding each said LED substrate are comprised of a screw and offset nut combination.

\* \* \* \* \*